United States Patent [19]

Merkle et al.

[11] B 4,013,684

[45] Mar. 22, 1977

[54] PREPARATION OF 2,5-DIMETHYLFURAN-3-CARBOXYLIC AMIDES

[75] Inventors: Hans Rupert Merkle, Ludwigshafen; Hardo Siegel, Speyer, both of Germany

[73] Assignee: Badische Anilin- & Soda-Fabrik Aktiengesellschaft, Ludwigshafen (Rhine), Germany

[22] Filed: May 14, 1973

[21] Appl. No.: 359,768

[44] Published under the second Trial Voluntary Protest Program on March 30, 1976 as document No. B 359,768.

[30] Foreign Application Priority Date

June 7, 1972 Germany .......................2227547

[52] U.S. Cl. .......................... 260/347.3; 260/347.5
[51] Int. Cl.$^2$ ........................................ C07D 307/66
[58] Field of Search ............................... 260/347.3

[56] References Cited

UNITED STATES PATENTS 3,806,506   4/1974   Felaver et al. .................. 260/347.3

OTHER PUBLICATIONS

Dunlop et al., "The Furans," 1953, p. 642.
Surrey, "Knoeven Agel Reaction," 1954, pp. 103–104.
Gonzaloz et al., Chem. Abst., Vol. 49, Col. 5422, (1955).

*Primary Examiner*—Harry I. Moatz
*Attorney, Agent, or Firm*—Johnston, Keil, Thompson & Shurtleff

[57] ABSTRACT

New and valuable process for the production of 2,5-dimethylfuran-3-carboxylic amides by reaction of acyloxypropionaldehyde with acetoacetamide.

4 Claims, No Drawings

PREPARATION OF 2,5-DIMETHYLFURAN-3-CARBOXYLIC AMIDES

The present invention relates to a process for the production of 2,5-dimethylfuran-3-carboxylic amides in very good yields.

It is known from German Patent No. 1,768,686 and German Laid-Open Application DOS Nos. 2,019,535 and 2,006,471 that furan-3-carboxamides are excellent pesticides having a very good fungicidal action.

It is known to produce furan-3-carboxylic acid derivatives by condensation of β-keto acid derivatives with α-hydroxyketones in the presence of Friedel-Crafts catalysts (Advance Heterocycl. Chem., 7, 377, 1966 or German Laid-Open Application DOS No. 2,006,471). A disadvantage of this method is that a large amount of catalyst is required for the reaction, making it difficult to isolate the product upon completion of the reaction. Furthermore, the catalyst attacks the hydroxyl groups in the α-hydroxyketone with the formation of by-products.

A further route (Beilstein, 3, 754; 197; II 273 and Chem. Ber., 85, 457, 1952) yields the ethyl ester of 2,5-dimethylfurancarboxylic acid by alkylation of sodium ethyl acetoacetate with chloroacetone and subsequent acid-catalyzed cyclization of the ethyl α-acetonylacetoacetate. This method is elaborate and difficult to carry out on an industrial scale. The same applies to the production of 2,5-dimethylfuran-3-carboxylic acid by heating pyruvic acid or tartaric acid in accordance with Beilstein, 18, 297, II 273.

We have now found that a 2,5-dimethylfurancarboxylic amide of the formula

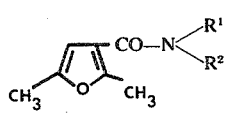

where $R^1$ and $R^2$ are identical or different and each denotes hydrogen, phenyl, substituted phenyl (substituted for example by linear or branched $C_1$ to $C_4$ alkyl, $C_1$ to $C_3$ alkoxy, acyloxy, alkylthio, halogen, haloalkyl, aryl), cycloalkyl, preferably cyclohexyl, substituted cyclohexyl (substituted for example by linear or branched $C_1$ to $C_4$ alkyl, halogen, alkoxy, alkylthio, acyloxy, aryloxy), alkenyl, cycloalkenyl, alkynyl, bicycloalkyl, e.g., norbornyl, or lower ($C_1$ to $C_4$) alkyl, is obtained in a simple manner by reacting an α-acyloxypropionaldehyde of the formula

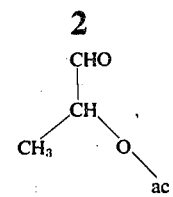

where ac denotes acyl (formyl, propionyl, butyryl, isobutyryl, preferably acetyl), with acetoacetamide of the formula

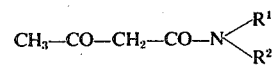

where $R^1$ and $R^2$ have the above meanings, in the presence of an acid catalyst.

The reaction may be represented as follows:

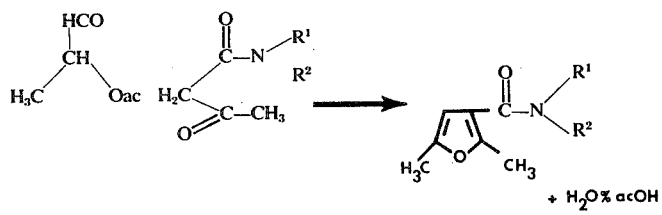

The α-acyloxypropionaldehyde may be easily prepared by hydroformylation of the corresponding vinyl ester.

The reaction is advantageously carried out by allowing the α-acyloxypropionaldehyde to react with the acetoacetamide in a solvent, e.g., benzene, toluene, xylene, cyclohexane, tetrahydrofuran, methanol, ethanol and methylene chloride, in the presence of 0.005 to 25% by weight, with reference to α-acyloxypropionaldehyde, of an organic or inorganic acid, e.g., p-toluenesulfonic acid, $H_2SO_4$, $H_3PO_4$, HCl, HI, HBr, or in the presence of an acid ion exchanger.

Acid catalysts are, quite generally, all proton-donating compounds which are acids in accordance with Bronsted's definition; all Lewis acids, e.g., $ZnCl_2$ and $AlCl_3$, are equally effective.

The reaction may be carried out at temperatures of from −10° to +180°C.

The α-acyloxypropionaldehyde is expediently employed in stoichiometric amounts or in an excess (10 to 15%).

The 2,5-dimethylfuran-3-carboxylic amides may be prepared at atmospheric pressure, or superatmospheric pressure in an inert gas atmosphere up to, for example, 700 atmospheres gauge.

The following examples illustrate the process of the invention.

EXAMPLE 1

2,5-dimethylfuran-3-carboxylic cyclohexylamide 24 parts (by weight) of α-acetoxypropionaldehyde is stirred with 36.6 parts of acetoacetic cyclohexylamide and 1 part of concentrated $H_2SO_4$ in 100 parts of toluene for 3 hours at 50°C. After the mixture has been cooled to room temperature it is washed with sodium hydrogen carbonate. The organic phase is dried with $Na_2SO_4$ and concentrated to dryness. There is obtained 41 parts of 2,5-dimethylfuran-3-carboxylic cyclohexylamide having a melting point of 111° to 113°C. After recrystallization from cyclohexane the compound melts at 114° to 115°C.

EXAMPLE 2

2,5-dimethylfuran-3-carboxanilide

A solution of 24 parts of α-acetoxypropionaldehyde, 35.4 parts of acetoacetanilide and 2 parts of p-toluenesulfonic acid in 100 parts of benzene is kept for 3 hours at 40°C and then boiled under reflux for 1 hour. Adopting the isolation procedure described in Example 1 there is obtained 41.8 parts of 2,5-dimethylfuran-3-carboxanilide having a melting point of 92° to 93°C.

EXAMPLE 3

In a high-pressure vessel 24 parts of α-acetoxypropionaldehyde, 36.6 parts of acetoacetanilide and 0.25 part of p-toluenesulfonic acid are dissolved in 300 parts of benzene. Carbon monoxide is then pressured in at 100 atmospheres gauge in the cold state and the contents of the vessel heated to 120°C. The pressure is subsequently increased to 700 atmospheres gauge. Pressure and temperature are then kept constant for 6 hours. The mixture is allowed to cool under pressure and the pressure is then released. The solvent is removed by distillation and the residue extracted with heptane. There is obtained 28 parts of 2,5-dimethylfuran-3-carboxanilide melting at 92° to 93°C.

What we claim is:

1. A process for the production of a 2,5-dimethylfurancarboxylic amide of the formula

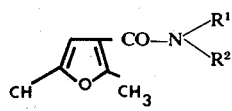

where $R^1$ and $R^2$ are identical or different and each denotes hydrogen, phenyl, substituted phenyl, cycloalkyl, substituted cyclohexyl, alkenyl, cycloalkenyl, alkynyl, bicycloalkyl or alkyl of 1 to 4 carbon atoms, wherein an α-acyloxypropionaldehyde of the formula

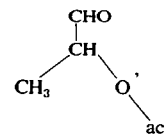

where ac denotes formyl, acetyl, propionyl, butyryl or isobutyryl, is reacted with an acetoacetamide of the formula

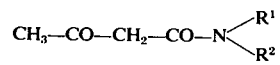

where $R^1$ and $R^2$ have the above meanings, in the presence of 0.005 to 25% by weight, with reference to the α-acyloxypropionaldehyde, of an acid catalyst selected from the group consisting of sulfuric acid and p-toluenesulfonic acid.

2. A process as claimed in claim 1 wherein the reaction is carried out at −10° to +180°C.

3. A process as claimed in claim 1 wherein $R^1$ is phenyl and $R^2$ is hydrogen.

4. A process as claimed in claim 1 wherein $R^1$ is cyclohexyl and $R^2$ is hydrogen.

* * * * *

UNITED STATES PATENT AND TRADEMARK OFFICE
CERTIFICATE OF CORRECTION

PATENT NO. : 4,013,684
DATED : March 22, 1977
INVENTOR(S) : MERKLE et al

It is certified that error appears in the above-identified patent and that said Letters Patent are hereby corrected as shown below:

In Column 3, the first formula in Claim 1, delete

" 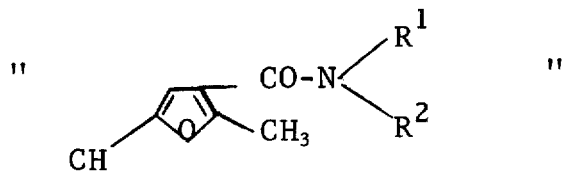 "

and substitute

-- 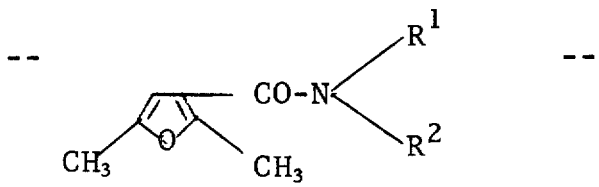 --

Signed and Sealed this

*Twenty-fifth* Day of *October 1977*

[SEAL]

Attest:

RUTH C. MASON
*Attesting Officer*

LUTRELLE F. PARKER
*Acting Commissioner of Patents and Trademarks*